(12) United States Patent
Kadosh et al.

(10) Patent No.: US 8,158,146 B2
(45) Date of Patent: Apr. 17, 2012

(54) STABLE COMBINATIONS OF AMLODIPINE BESYLATE AND BENAZEPRIL HYDROCHLORIDE

(75) Inventors: Mali Kadosh, Moshav Sday Hemed (IL); Fanny Leska, Herzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1514 days.

(21) Appl. No.: 11/238,496

(22) Filed: Sep. 28, 2005

(65) Prior Publication Data

US 2007/0071811 A1    Mar. 29, 2007

(51) Int. Cl.
*A61K 9/20* (2006.01)

(52) U.S. Cl. ............... 424/464; 514/355; 514/212.07

(58) Field of Classification Search .................. None
See application file for complete search history.

(56) References Cited

U.S. PATENT DOCUMENTS

| | | | |
|---|---|---|---|
| 4,808,413 A | 2/1989 | Joshi et al. | |
| 4,873,235 A | 10/1989 | Parsons et al. | |
| 5,202,322 A | 4/1993 | Allen et al. | |
| 5,593,696 A | 1/1997 | McNally et al. | |
| 5,948,799 A | 9/1999 | Cropp | |
| 6,162,802 A | 12/2000 | Papa et al. | |
| 6,245,787 B1 | 6/2001 | Cropp et al. | |
| 6,521,647 B2 | 2/2003 | Foster | |
| 2002/0176889 A1 | 11/2002 | Lemmens et al. | |
| 2002/0183308 A1 | 12/2002 | Sherman | |
| 2004/0001886 A1 | 1/2004 | Chakole et al. | |
| 2005/0220877 A1 | 10/2005 | Patel et al. | |
| 2006/0009502 A1 | 1/2006 | Horiuchi et al. | |
| 2006/0257482 A1 | 11/2006 | Kumar et al. | |
| 2007/0009614 A1 | 1/2007 | Stokes | |
| 2007/0059367 A1 | 3/2007 | Cherukuri | |
| 2007/0134321 A1 | 6/2007 | Solomon et al. | |
| 2008/0194542 A1 | 8/2008 | Vithalapuram et al. | |
| 2008/0268049 A1 | 10/2008 | Dhaliwal et al. | |

FOREIGN PATENT DOCUMENTS

| | | |
|---|---|---|
| EP | 0244944 | 11/1987 |
| GB | 2394660 A | 5/2004 |
| WO | WO 99/18957 | 4/1999 |
| WO | 01/13900 A2 | 3/2001 |
| WO | 01/15674 A2 | 3/2001 |
| WO | 02/40007 A1 | 5/2002 |
| WO | WO 02/49645 A | 6/2002 |
| WO | WO 02/49646 A | 6/2002 |
| WO | 2004/112788 A1 | 12/2004 |
| WO | 2005/018561 A2 | 3/2005 |
| WO | 2005/030217 A1 | 4/2005 |
| WO | 2005/037278 A2 | 4/2005 |

OTHER PUBLICATIONS

K. Raghu Naidu et al. "Stability indicating RP-HPLC method for simultaneous determination of amlodipine and benazepril hydrochloride from their combination drug product" Journal of Pharmaceutical and Biomedical Analysis, New York, New York, US, vol. 39, No. 1-2, Sep. 1, 2005, pp. 147-155.

*Primary Examiner* — Robert A Wax
*Assistant Examiner* — Hasan S Ahmed
(74) *Attorney, Agent, or Firm* — Kenyon & Kenyon LLP

(57) ABSTRACT

The present invention provides a pharmaceutical composition comprising benazepril and amlodipine wherein the benazepril and the amlodipine are in physical contact with one another, and methods for making the same.

21 Claims, 1 Drawing Sheet

Amlodipine Besylate and Benazepril Hydrochloride Capsules

STABLE COMBINATIONS OF AMLODIPINE BESYLATE AND BENAZEPRIL HYDROCHLORIDE

FIELD OF INVENTION

The present invention relates to the field of combination therapy of amlodipine with benazepril.

BACKGROUND OF THE INVENTION

In the fight against cardiovascular disease, our current arsenal of weapons includes angiotensin converting enzyme inhibitors (ACEI) and calcium channel blockers (CCB). Combination therapy of an ACEI with a CCB can achieve synergistic results effective in treating a variety of conditions including hypertension, congestive heart failure, angina, myocardial infarction, atherosclerosis, diabetic nephropathy, diabetic cardiac myopathy, renal insufficiency, peripheral vascular disease, left ventricular hypertrophy, cognitive dysfunction, stroke, and headache. The combination of the ACEI benazepril and the CCB amlodipine is described by U.S. Pat. No. 6,162,802 ("the '802 patent").

Benazepril can be administered as benazepril hydrochloride, which is chemically identified as 3-[[1-(ethoxycarbonyl)-3-phenyl-(1S)-propyl]amino]-2,3,4,5-tetrahydro-2-oxo-1H-1-(3S)-benzazepine-1-acetic acid monohydrochloride ($C_{24}H_{28}N_2O_5 \cdot HCl$). Amlodipine can be administered as amlodipine besylate, which is chemically identified as (R.S.) 3-ethyl-5-methyl-2-(2-aminoethoxymethyl)-4-(2-chlorophenyl)-1,4-dihydro-6-methyl-3,5-pyridinedicarboxylate benzenesulphonate ($C_{20}H_{25}ClN_2O_5 \cdot AC_6H_6O_3S$). A combination of benazepril hydrochloride and amlodipine besylate is marketed in the United States by Novartis under the trade name LOTREL® as capsules for oral administration. The capsules are formulated in four different strengths with an amount of amlodipine besylate equivalent to 2.5 mg, 5 mg, or 10 mg of amlodipine free base, and 10 mg or 20 mg of benazepril hydrochloride providing for the following available combinations: 2.5/10 mg, 5/10 mg, 5/20 mg, and 10/20 mg. LOTREL® is indicated for the treatment of hypertension.

The '802 patent teaches that "[b]enazepril and amlodipine are physically incompatible substances. Hence, if incorporated into a single dosage form they must be kept physically separated." Col. 3, lines 48-50.

The present inventors have surprisingly discovered a method for making a pharmaceutical composition containing both amlodipine and benazepril wherein physical separation of the two drug components is not required. Such a pharmaceutical composition and methods for making it are provided herein.

SUMMARY OF THE INVENTION

In one embodiment, the present invention provides a stable pharmaceutical composition comprising benazepril, solvates, esters, or pharmaceutically acceptable salts thereof, and amlodipine or solvates, esters, or pharmaceutically acceptable salts thereof. The pharmaceutical composition is stable, that is, after storage for about 3 months at about 40° C. at about 75% relative humidity, it contains no more than 2.5% of (s,s)-diacid by weight relative to the benazepril and/or no more than 0.3% of impurity D by weight relative to the amlodipine. Preferably, the benazepril is benazepril hydrochloride, and the amlodipine is amlodipine besylate.

In a preferred embodiment, the benazepril and the amlodipine are in physical contact with one another.

In another embodiment, the benazepril hydrochloride is prepared by wet granulation, and the amlodipine besylate is prepared by dry processing.

In another embodiment, the present invention provides a method including the steps of: preparing a benazepril composition by wet granulation; preparing an amlodipine composition by dry processing; and contacting the benazepril composition and the amlodipine composition to obtain a combination pharmaceutical composition.

Wet granulation preferably includes the steps of combining benazepril hydrochloride with one or more pharmaceutical excipients preferably selected from the group consisting of pregelatinized starch, lactose monohydrate, starch, crospovidone, and microcrystalline cellulose; adding a granulation solution to obtain a wet granulate, wherein the granulation solution comprises water and optionally, polysorbate 80, povidone, or both; drying the wet granulate to obtain a dry granulate; and milling the dry granulate.

Dry processing preferably includes the steps of sieving a mixture of amlodipine besylate with one or more pharmaceutical excipients preferably selected from the group consisting of calcium phosphate dibasic, sodium starch glycolate, microcrystalline cellulose, and colloidal silicon dioxide; and blending the mixture.

In one embodiment, dry processing further includes sieving one or more additional pharmaceutical excipients, preferably crospovidone and/or magnesium stearate, and blending the additional pharmaceutical excipient with the mixture.

In another embodiment, the method includes a step of encapsulating the combination pharmaceutical composition.

In one embodiment, the present invention provides a benazepril composition comprising about 5% to about 20% benazepril hydrochloride, about 15% to about 20% pregelatinized starch, about 25% to about 35% lactose monohydrate, about 10% to about 15% starch, about 5% crospovidone, about 15% to about 25% microcrystalline cellulose, about 0.1% to about 2% polysorbate 80, and about 5% povidone, by weight percent relative to the total benazepril composition.

In another embodiment, the present invention provides an amlodipine composition comprising about 2% to about 10% amlodipine besylate, about 25% to about 30% calcium phosphate dibasic, about 1% to about 2% sodium starch glycolate, about 50% to about 60% microcrystalline cellulose, about 1% colloidal silicon dioxide, about 5% crospovidone, and about 0.2% to about 2% magnesium stearate, by weight percent relative to the total amlodipine composition.

DETAILED DESCRIPTION OF THE INVENTION

Figure 1:
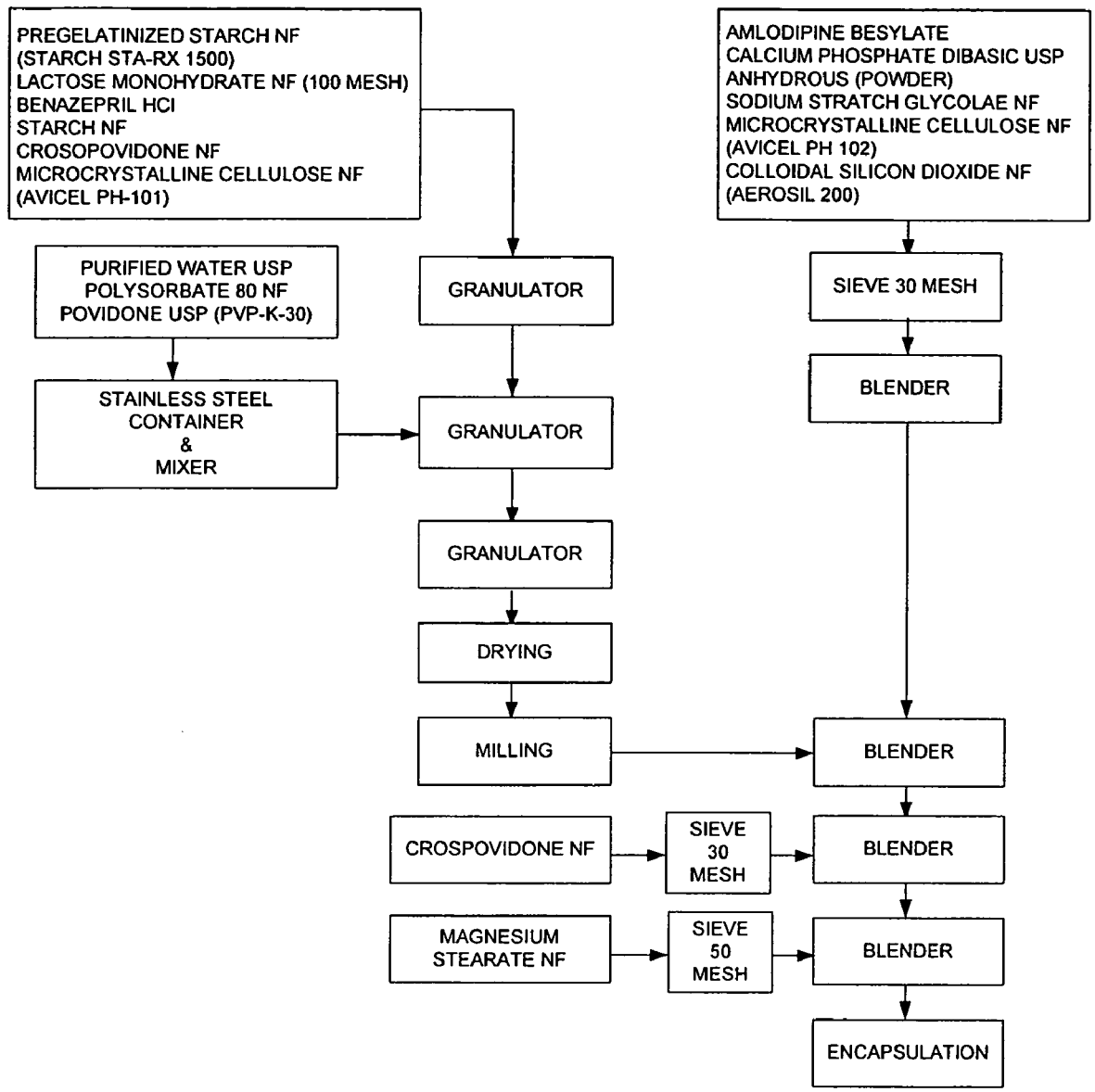
FIG. 1 illustrates a flowchart for a method for making a capsule comprising a mixture of benazepril and amlodipine.

In one embodiment, the present invention provides a stable pharmaceutical composition comprising benazepril, solvates, esters, or pharmaceutically acceptable salts thereof, and amlodipine, solvates, esters, or pharmaceutically acceptable salts thereof. The general term amlodipine as used herein refers to the free base form. In the stable pharmaceutical compositions of the present invention, the benazepril is preferably benazepril hydrochloride, and the amlodipine is preferably amlodipine besylate.

The pharmaceutical composition is stable, that is, the pharmaceutical composition contains low levels of degradation products. In part, the composition slows and/or avoids the degradation of the active ingredient, thereby reducing the amounts of impurities present in the active ingredient after storage. A main degradation product of benazepril is (s,s)-diacid (benazeprilat), which is the active metabolite of benazepril. A main degradation product of amlodipine is impurity D (-ethyl 5-methyl 2-[(2-aminoethoxy)methyl]-4-(2-chlorophenyl)-6-methylpyridine-3,5-dicarboxylate). The specifications for degradation products of benazepril and amlodipine are summarized in Table 1.

TABLE 1

Limits for Degradation Products of Benazepril and Amlodipine

Benazepril HCl
Limits are by weight percent relative to the labeled
amount of benazepril HCl.

| | |
|---|---|
| (S,S)-diacid | no more than 2.5% |
| Any other impurity | no more than 0.2% |
| Total other impurities (excluding (s,s)-diacid) | no more than 1.0% |

Amlodipine
Limits are by weight percent relative to the labeled amount of amlodipine.

| | |
|---|---|
| Impurity D | no more than 0.3% |
| Any other impurity | no more than 0.2% |
| Total other impurities (excluding Impurity D) | no more than 1.0% |

In one embodiment, after the pharmaceutical composition is stored for about 3 months at about 40° C. at about 75% relative humidity, the pharmaceutical composition contains no more than 2.5% of (s,s)-diacid by weight relative to the benazepril and/or no more than 0.3% of impurity D by weight relative to the amlodipine.

In a preferred embodiment, the benazepril and the amlodipine are in physical contact with one another. Examples of physical contact include physical contact at an uncoated interface between tablet layers, physical contact within the fluid medium of a liquid oral or injectable dosage form, and physical contact throughout a blended mixture of the two active ingredients. In a preferred embodiment, a blended mixture comprising the two active ingredients is used as a capsule filling.

The pharmaceutical composition preferably contains about 10 mg to about 20 mg benazepril hydrochloride, more preferably about 10 mg or about 20 mg. Preferably, the amount of amlodipine besylate corresponds to about 2.5 mg to about 10 mg of amlodipine free base. More preferably, the amount of amlodipine besylate corresponds to about 2.5 mg, about 5 mg, or about 10 mg of amlodipine free base. Preferably, the ratio of benazepril to amlodipine corresponds to a weight ratio of about 2:1 to about 4:1, more preferably about 2:1 or about 4:1.

In one embodiment, the benazepril hydrochloride is prepared by wet granulation, and the amlodipine besylate is prepared by dry processing. Wet granulation and dry processing are described in further detail below.

In one embodiment, the present invention provides a method for making a pharmaceutical composition comprising both benazepril and amlodipine. The pharmaceutical composition comprising both benazepril and amlodipine is referred to as the combination pharmaceutical composition. The method includes the steps of: preparing a benazepril composition by wet granulation; preparing an amlodipine composition by dry processing; and contacting the benazepril composition and the amlodipine composition to obtain a combination pharmaceutical composition. FIG. 1 depicts a preferred embodiment of this method.

Wet granulation preferably includes the steps of combining benazepril hydrochloride with one or more pharmaceutical excipients; adding a granulation solution to obtain a wet granulate, wherein the granulation solution preferably comprises water and optionally, one or more additional excipients; drying the wet granulate to obtain a dry granulate; and milling the dry granulate. Pharmaceutical excipients are described in further detail below. For the benazepril composition, preferred pharmaceutical excipients include pregelatinized starch, lactose monohydrate, starch, crospovidone, microcrystalline cellulose, polysorbate 80, and povidone.

Dry processing preferably includes the steps of sieving a mixture of amlodipine besylate with one or more pharmaceutical excipients; and blending the mixture. If necessary, the sieving step is performed to avoid the inclusion of agglomerates and extraneous matter. For the amlodipine composition, preferred pharmaceutical excipients include calcium phosphate dibasic, sodium starch glycolate, microcrystalline cellulose, and colloidal silicon dioxide. Preferably, the mixture is sieved through a size 30 mesh.

In one embodiment, dry processing further includes sieving one or more additional pharmaceutical excipients and blending the additional pharmaceutical excipient with the mixture, i.e., the amlodipine composition. In a preferred embodiment, the additional pharmaceutical excipient(s) are blended with the amlodipine composition after it is combined with the benazepril composition. Preferred additional pharmaceutical excipients include crospovidone and magnesium stearate. Preferably, crospovidone is sieved through a size 30 mesh. Preferably, magnesium stearate is sieved through a size 50 mesh.

In one embodiment, the method includes a step of encapsulating the combination pharmaceutical composition.

In a preferred embodiment, the method includes the steps of combining benazepril hydrochloride with one or more pharmaceutical excipients selected from the group consisting of pregelatinized starch, lactose monohydrate, starch, crospovidone, and microcrystalline cellulose; adding a granulation solution to obtain a wet granulate, wherein the granulation solution comprises water, polysorbate 80, and povidone; drying the wet granulate to obtain a dry granulate; milling the dry granulate; sieving a mixture of amlodipine besylate and one or more pharmaceutical excipients selected from the group consisting of calcium phosphate dibasic, sodium starch glycolate, microcrystalline cellulose, and colloidal silicon dioxide through a 30 mesh sieve; blending the mixture with the dry granulate to form a combined pharmaceutical composition; sieving crospovidone through a 30 mesh sieve; blending the crospovidone with the combined pharmaceutical composition; sieving magnesium stearate through a 50 mesh sieve; blending the magnesium stearate with the combined pharmaceutical composition; and encapsulating the combined pharmaceutical composition.

In one embodiment, the present invention provides a benazepril composition comprising about 5% to about 20% benazepril hydrochloride, about 15% to about 20% pregelatinized starch, about 25% to about 35% lactose monohydrate, about 10% to about 15% starch, about 5% crospovidone, about 15% to about 25% microcrystalline cellulose, about 0.1% to about 2% polysorbate 80, and about 5% povidone, by weight percent relative to the total benazepril composition.

In another embodiment, the present invention provides an amlodipine composition comprising about 2% to about 10% amlodipine besylate, about 25% to about 30% calcium phosphate dibasic, about 1% to about 2% sodium starch glycolate, about 50% to about 60% microcrystalline cellulose, about 1% colloidal silicon dioxide, about 5% crospovidone, and about 0.2% to about 2% magnesium stearate, by weight percent relative to the total amlodipine composition.

The compositions of the present invention can be prepared as medicaments to be administered e.g. orally. Suitable forms for oral administration include solid forms such as tablets, powders, granulates, capsules.

In addition to the active ingredient(s), the compositions of the present invention can contain one or more excipients or adjuvants. An excipient is an inert ingredient added to a pharmaceutical composition to dilute it or to give it form or consistency. An adjuvant assists the action of an active ingredient. Selection of excipients and adjuvants and the amounts to use can be readily determined by the formulation scientist based upon experience and consideration of standard procedures and reference works in the field.

Diluents increase the bulk of a solid pharmaceutical composition, and can make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dibasic calcium phosphate dihydrate, tribasic calcium phosphate, mannitol, powdered cellulose and sorbitol.

Solid pharmaceutical compositions that are compacted into a dosage form, such as a tablet, can include excipients whose functions include helping to bind the active ingredient and other excipients together after compression. Binders for solid pharmaceutical compositions include carboxymethylcellulose sodium, ethyl cellulose, gelatin, hydroxyethyl cellulose, hydroxypropyl cellulose (e.g. Klucel®), hydroxypropyl methyl cellulose (e.g. Methocel®), methylcellulose, povidone (e.g. Kollidon®, Plasdone®), pregelatinized starch, and starch.

The dissolution rate of a compacted solid pharmaceutical composition in the patient's stomach can be increased by the addition of a disintegrant to the composition. Disintegrants include carboxymethylcellulose calcium, croscarmellose sodium (e.g. Ac-Di-Sol®), crospovidone (e.g. Kollidon®, Polyplasdone®), microcrystalline cellulose, polacrilin potassium, pregelatinized starch, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch and talc.

When a dosage form such as a tablet is made by the compaction of a powdered composition, the composition is subjected to pressure, e.g., from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium lauryl sulfate, sodium stearyl fumarate, stearic acid, talc, and zinc stearate.

The dosage form of the present invention can be a capsule containing the composition, preferably a powdered and/or granulated solid composition of the invention, within either a hard or soft shell. The shell can be made from gelatin and optionally contain a plasticizer such as glycerin and sorbitol, and an opacifying agent or colorant.

Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

A composition for tableting or capsule filling can be prepared by wet granulation. In wet granulation, some or all of the active ingredients and excipients in powder form are blended and then further mixed in the presence of a liquid, typically water that causes the powders to clump into granules. The granulate is screened and/or milled, dried, screened and/or milled to the desired particle size. The granulate can then be filled into capsules optionally with other ingredients. This process is the preferred process for the Benazepril component of the present invention.

A granular composition can be prepared conventionally by dry granulation. For example, the blended composition of the actives and excipients can be compacted into a slug or a sheet and then comminuted into compacted granules. The compacted granules can subsequently be compressed into a tablet or filled into capsules. This technique is more suitable for the amlodipine component of the instant invention but even more preferred is the use of a blended powder composition of the amlodipine and excipients.

A capsule filling of the present invention can comprise any of the aforementioned blends and granulates that were described above, however, most preferred is a capsule containing a benazepril granulate prepared by wet granulation, mixed with a dry blended powder composition of the amlodipine and excipients.

Having thus described the present invention with reference to certain preferred embodiments, the invention will now be further illustrated by the following non-limiting examples.

EXAMPLES

Example 1

Amlodipine Besylate/Benazepril Hydrochloride Capsules

Capsules containing both benazepril hydrochloride and amlodipine besylate were made by the following process.

Preparation of Benazepril Hydrochloride Granulate—Part I:

The following materials were mixed in a granulator mixer: pregelatinized starch (Starch STA-RX-1500), lactose monohydrate NF (100 mesh), benazepril hydrochloride, starch NF, crospovidone NF, and microcrystalline cellulose NF (Avicel PH 101). The granulation solution was prepared by adding purified water USP to a mixture of polysorbate 80 NF and PVP K-30 (povidone USP) while mixing and continuing to mix until dissolved. The granulation solution was then added to the granulator mixer and mixed until a granulate was obtained. The granulate was then dried in a fluid bed drier.

The dried granulate was then milled in an oscillating granulator and placed in a container.

Dry Mix (Amlodipine)—Part II:

The following materials were sieved: amlodipine besylate, calcium phosphate dibasic USP anhydrous (powder) and sodium starch glycolate NF. The sieved materials were then transferred to a blender and blended. Microcrystalline cellulose and colloidal silicon dioxide were sieved, added to the mixture in the blender, and mixed. The mixture was then removed to a container.

Combination of Amlodipine and Benazepril Hydrochloride—Part III:

The granulate from part I and the dry mixture from part II were placed in a blender and blended. Crospovidone was sieved and added to the blender and the mixture blended. Magnesium stearate was then sieved and added to the blender and the mixture was blended.

Encapsulation—Part IV:

The final blend of part III was filled into capsules. Specific compositions are described in Table 2.

TABLE 2

Amlodipine Besylate/Benazepril Hydrochloride Capsules

| Ingredient | Amlodipine/Benazepril (mg) per capsule | | | |
|---|---|---|---|---|
| | 2.5 mg/10 mg | 5 mg/10 mg | 5 mg/20 mg | 10 mg/20 mg |
| Benazepril granulate: | 130.5 | 130.5 | 130.5 | 130.5 |
| Benazepril HCl | 10.0 | 10.0 | 20.0 | 20.0 |
| Pregelatinized Starch NF (Starch STA-RX 1500) | 24.0 | 24.0 | 22.0 | 22.0 |
| Lactose Monohydrate NF (100 mesh) | 39.2 | 39.2 | 35.2 | 35.2 |
| Starch NF | 16.0 | 16.0 | 15.0 | 15.0 |
| Crospovidone NF | 7.0 | 7.0 | 7.0 | 7.0 |
| Microcrystalline Cellulose NF (Avicel PH-101) | 27.0 | 27.0 | 24.0 | 24.0 |
| Granulation solvent: | | | | |
| Polysorbate 80 NF | 0.8 | 0.8 | 0.8 | 0.8 |
| Povidone USP (PVP K-30) | 6.5 | 6.5 | 6.5 | 6.5 |
| Purified Water USP | * | * | * | * |
| Amlodipine composition: | 139.5 | 139.5 | 139.5 | 139.5 |
| Amlodipine Besylate | 3.465** | 6.93** | 6.93** | 13.86** |
| Calcium Phosphate Dibasic USP Anhydrous (powder) | 40.0 | 39.0 | 39.0 | 37.0 |
| Sodium Starch Glycolate NF | 2.0 | 2.0 | 2.0 | 2.0 |
| Microcrystalline Cellulose NF (Avicel PH-102) | 83.135 | 80.67 | 80.67 | 75.74 |
| Colloidal Silicon Dioxide NF (Aerosil 200) | 1.4 | 1.4 | 1.4 | 1.4 |
| Added after combining with benazepril composition: | | | | |
| Crospovidone NF (30 mesh) | 7.0 | 7.0 | 7.0 | 7.0 |
| Magnesium Stearate NF (50 mesh) | 2.5 | 2.5 | 2.5 | 2.5 |
| Total | 270.0 | 270.0 | 270.0 | 270.0 |

* For granulation processing only.
**3.465 mg, 6.93 mg, and 13.86 mg of amlodipine besylate correspond to 2.5 mg, 5 mg, and 10 mg of amlodipine free base, respectively.

Example 2

Stability Study

Over the course of 3 months at 40° C. and 75% relative humidity, the degradation products of the amlodipine besylate/benazepril hydrochloride capsules were measured by HPLC. Results are summarized in Table 3 below.

TABLE 3

Stability Results for Amlodipine Besylate/Benazepril Hydrochloride Capsules

| | Time | 1M | | | 2M | | | 3M | | |
|---|---|---|---|---|---|---|---|---|---|---|
| | zero | 40 c/75% RH | | | 40 c/75% RH | | | 40 c/75% RH | PP CAP | PP CAP |
| 2.5/10 mg *s,s-diacid | | 100 Tabs | 100 Tabs | 1000 Tabs | 100 Tabs | 100 Tabs | 1000 Tabs | 100 Tabs | 100 Tabs | 1000 Tabs |
| Total(excl*) | | CRC[1] | PP CAP[2] | PP CAP | CRC | PP CAP | PP CAP | CRC | PP CAP | PP CAP |
| **Impurity D | <0.05 | 0.08 | — | — | 0.06 | — | — | 0.1 | — | — |
| Total(excl*) | <0.05 | <0.05 | — | — | <0.05 | — | — | <0.05 | — | — |

TABLE 3-continued

Stability Results for Amlodipine Besylate/Benazepril Hydrochloride Capsules

| | | Time | 1M | | | 2M | | | 3M | | |
|---|---|---|---|---|---|---|---|---|---|---|---|
| | | zero | 40 c/75% RH | | | 40 c/75% RH | | | 40 c/75% RH | PP CAP | PP CAP |
| 5/10 mg | *s,s-diacid | <0.05 | 0.3 | 0.4 | 0.4 | 0.6 | 1.1 | 0.8 | 1.0 | 1.2 | 1.2 |
| | Total(excl*) | 0.07 | 0.1 | 0.1 | 0.1 | 0.2 | 0.2 | 0.2 | 0.2 | 0.2 | 0.2 |
| | **Impurity D | <0.05 | 0.1 | 0.1 | 0.1 | 0.08 | 0.1 | 0.08 | 0.1 | 0.1 | 0.1 |
| | Total(excl*) | <0.05 | <0.05 | <0.05 | <0.05 | <0.05 | <0.05 | <0.05 | <0.05 | <0.05 | <0.05 |
| 5/20 mg | *s,s-diacid | <0.05 | 0.2 | 0.3 | 0.2 | 0.4 | 0.6 | 0.4 | 0.8 | 1.0 | 0.8 |
| | Total(excl*) | 0.06 | 0.05 | 0.06 | 0.05 | 0.1 | 0.1 | 0.1 | 0.1 | 0.1 | 0.1 |
| | **Impurity D | <0.05 | 0.1 | 0.1 | 0.1 | 0.06 | 0.08 | 0.07 | 0.1 | 0.09 | 0.1 |
| | Total(excl*) | <0.05 | <0.05 | <0.05 | <0.05 | <0.05 | <0.05 | <0.05 | 0.06 | 0.07 | 0.08 |
| 10/20 mg | *s,s-diacid | <0.05 | 0.2 | — | — | 0.3 | — | — | 0.6 | — | — |
| | Total(excl*) | 0.07 | 0.1 | — | — | 0.1 | — | — | 0.2 | — | — |
| | **Impurity D | <0.05 | 0.06 | — | — | 0.06 | — | — | 0.1 | — | — |
| | Total(excl*) | <0.05 | <0.05 | — | — | <0.05 | — | — | <0.05 | — | — |

*s,s diacid results from degradation of Benazepril
**Impurity D results from degradation of Amlodipine
[1]CRC = Child resistant Cap
[2]PP CAP = Polypropylene Cap

What is claimed is:

1. A pharmaceutical composition comprising:
   a) benazepril or its solvates, or a pharmaceutically acceptable salt thereof, and
   b) amlodipine or its solvates, or a pharmaceutically acceptable salt thereof, wherein the benazepril and the amlodipine are in physical contact with one another, and wherein after about 3 months at about 40° C. at about 75% relative humidity, the pharmaceutical composition contains:
      i) no more than 2.5% of (s,s)-diacid by weight relative to the benazepril; and/or
      ii) no more than 0.3% of impurity D by weight relative to the amlodipine.

2. The pharmaceutical composition of claim 1, wherein the pharmaceutical composition is encapsulated.

3. The pharmaceutical composition of claim 1, wherein the benazepril is benazepril hydrochloride.

4. The pharmaceutical composition of claim 1, wherein the amlodipine is amlodipine besylate.

5. The pharmaceutical composition of claim 1, wherein the benazepril is prepared by wet granulation, and the amlodipine is prepared by dry processing.

6. A method comprising:
   a) preparing a benazepril composition by wet granulation;
   b) preparing an amlodipine composition by dry processing; and
   c) physically contacting the benazepril composition and the amlodipine composition, to obtain a combination pharmaceutical composition.

7. The method of claim 6, wherein the benazepril composition comprises benazepril hydrochloride and one or more pharmaceutical excipients.

8. The method of claim 6, wherein the benazepril composition comprises benazepril and one or more pharmaceutical excipients selected from the group consisting of pregelatinized starch, lactose monohydrate, starch, crospovidone, microcrystalline cellulose, polysorbate 80, and povidone.

9. The method of claim 6, wherein the benazepril composition comprises:
   1) about 5% to about 20% benazepril hydrochloride;
   2) about 15% to about 20% pregelatinized starch;
   3) about 25% to about 35% lactose monohydrate;
   4) about 10% to about 15% starch;
   5) about 5% crospovidone;
   6) about 15% to about 25% microcrystalline cellulose;
   7) about 0.1% to about 2% polysorbate 80; and
   8) about 5% povidone,
   by weight percent relative to the total benazepril composition.

10. The method of claim 6, wherein preparing the benazepril composition by wet granulation comprises:
   a1) combining benazepril hydrochloride with one or more pharmaceutical excipients selected from the group consisting of pregelatinized starch, lactose monohydrate, starch, crospovidone, and microcrystalline cellulose;
   a2) adding a granulation solution to obtain a wet granulate, wherein the granulation solution comprises water;
   a3) drying the wet granulate to obtain a dry granulate; and
   a4) milling the dry granulate.

11. The method of claim 6, wherein the amlodipine composition comprises amlodipine besylate and one or more pharmaceutical excipients.

12. The method of claim 6, wherein the amlodipine composition comprises amlodipine and one or more pharmaceutical excipients selected from the group consisting of calcium phosphate dibasic, sodium starch glycolate, microcrystalline cellulose, and colloidal silicon dioxide.

13. The method of claim 6, wherein the amlodipine composition comprises:
   1) about 2% to about 10% amlodipine besylate;
   2) about 25% to about 30% calcium phosphate dibasic;
   3) about 1% to about 2% sodium starch glycolate;
   4) about 50% to about 60% microcrystalline cellulose;
   5) about 1% colloidal silicon dioxide,
   by weight percent relative to the total amlodipine composition.

14. The method of claim 6, further comprising: adding crospovidone and magnesium stearate in step c).

15. The method of claim 6, further comprising: adding in step c) about 1% to about 5% crospovidone and about 0.2% to about 2% magnesium stearate by weight percent relative to the total amlodipine composition.

16. The method of claim 6, wherein preparing the amlodipine composition by dry processing comprises:
   b1) sieving a mixture of amlodipine besylate and one or more pharmaceutical excipients selected from the group consisting of calcium phosphate dibasic, sodium starch glycolate, microcrystalline cellulose, and colloidal silicon dioxide; and
   b2) blending the mixture.

17. The method of claim 16, further comprising:
b3) sieving one or more additional pharmaceutical excipients selected from the group consisting of crospovidone and magnesium stearate; and
b4) blending the one or more additional pharmaceutical excipients with the mixture of step b2).

18. The method of claim 6, further comprising encapsulating the combination pharmaceutical composition.

19. A method comprising:
a) combining benazepril hydrochloride with one or more pharmaceutical excipients selected from the group consisting of pregelatinized starch, lactose monohydrate, starch, crospovidone, and microcrystalline cellulose;
b) adding a granulation solution to obtain a wet granulate, wherein the granulation solution comprises water, polysorbate 80, and povidone;
c) drying the wet granulate to obtain a dry granulate;
d) milling the dry granulate;
e) sieving a mixture of amlodipine besylate and one or more pharmaceutical excipients selected from the group consisting of calcium phosphate dibasic, sodium starch glycolate, microcrystalline cellulose, and colloidal silicon dioxide, through a 30 mesh sieve;
f) blending the mixture with the dry granulate to form a combined pharmaceutical composition;
g) sieving crospovidone through a 30 mesh sieve;
h) blending the crospovidone with the combined pharmaceutical composition;
i) sieving magnesium stearate through a 50 mesh sieve;
j) blending the magnesium stearate with the combined pharmaceutical composition; and
k) encapsulating the combined pharmaceutical composition.

20. The method of claim 6, further comprising adding excipients in step c).

21. The method of claim 10, wherein the granulation solution in step a2) further comprises at least one of polysorbate 80 and povidone.

* * * * *